(12) United States Patent
Batchelor et al.

(10) Patent No.: US 12,708,430 B2
(45) Date of Patent: Aug. 18, 2026

(54) INTRAUTERINE MORCELLATION DEVICE

(71) Applicant: GYRUS ACMI, INC., Westborough, MA (US)

(72) Inventors: Kester Julian Batchelor, Mound, MN (US); Charles A. Baker, Rogers, MN (US); Theodore C. Blus, Arden Hills, MN (US); Joey Magno, Cordova, TN (US); Jake Terravecchia, Brighton, MA (US); Jeffrey D. Holton, Stanchfield, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 203 days.

(21) Appl. No.: 18/494,882

(22) Filed: Oct. 26, 2023

(65) Prior Publication Data

US 2024/0307109 A1 Sep. 19, 2024

Related U.S. Application Data

(60) Provisional application No. 63/490,349, filed on Mar. 15, 2023.

(51) Int. Cl.
*A61B 18/14* (2006.01)
*A61B 1/303* (2006.01)
(Continued)

(52) U.S. Cl.
CPC .......... *A61B 18/1485* (2013.01); *A61B 1/303* (2013.01); *A61B 2017/00336* (2013.01); (Continued)

(58) Field of Classification Search
CPC ................ A61B 1/303; A61B 18/1485; A61B 2218/002; A61B 2017/00296; A61B 2017/00336; A61B 2017/00982
See application file for complete search history.

(56) References Cited

U.S. PATENT DOCUMENTS 5,423,813 A * 6/1995 Kaiser .................. A61B 18/149
606/46
10,682,174 B2 6/2020 Blanc
(Continued)

FOREIGN PATENT DOCUMENTS

| CN | 110393555 | 11/2019 |
|---|---|---|
| JP | 2009045429 | 3/2009 |
| JP | 2016516536 | 6/2016 |

OTHER PUBLICATIONS

"Japanese Application Serial No. 2024-41657, Notification of Reasons for Refusal mailed Apr. 28, 2026", w English Translation, 10 pgs.

*Primary Examiner* — Aaron B Fairchild
(74) *Attorney, Agent, or Firm* — Schwegman Lundberg & Woessner, P.A.

(57) ABSTRACT

A medical device can include an elongate member, an irrigation port at a proximal end of the elongate member, and a resection assembly. The elongate member defines a first track and a second track. The resection assembly extends from a distal end of the elongate member and has a first member, a second member, and an electrically activatable resection element extending from a distal end of the first member. The first member includes a first portion located along the first track. The second member has a first portion located along the second track and the second member includes a longitudinally axial fluid conduit passageway. The passageway is in fluid communication with the irrigation port.

14 Claims, 6 Drawing Sheets

(51) Int. Cl.
*A61B 17/00* (2006.01)
*A61B 18/00* (2006.01)

(52) U.S. Cl.
CPC ............... *A61B 2018/00083* (2013.01); *A61B 2018/00559* (2013.01); *A61B 2018/00982* (2013.01); *A61B 2218/002* (2013.01); *A61B 2218/007* (2013.01)

(56) References Cited

U.S. PATENT DOCUMENTS

| | | | | |
|---|---|---|---|---|
| 11,141,218 | B2 | 10/2021 | Hluchy | |
| 11,564,739 | B2 | 1/2023 | Jensrud et al. | |
| 2003/0130575 | A1 * | 7/2003 | Desai ............... | A61B 17/00234 600/417 |

* cited by examiner

INTRAUTERINE MORCELLATION DEVICE

PRIORITY CLAIM

This application claims the benefit of U.S. Provisional Patent Application No. 63/490,349, filed Mar. 15, 2023, the contents of which are hereby incorporated by reference in their entirety.

TECHNICAL FIELD

This document pertains generally, but not by way of limitation, to surgical devices that can be used for various surgical procedures. More specifically, but not by way of limitation, the present application relates to a surgical device that may be used to treat the reproductive system of a female patient.

BACKGROUND

Growths can occur in the lining of a uterus. This can cause discomfort and interfere with menstruation and fertility if left untreated. The growths can include polyps and fibroids. Uterine polyps are growths that can form in the inner lining of a uterus. Uterine polyps can form when an overgrowth of endometrial tissue occurs. The polyp can attach to the endometrium and then extend into the uterus.

Fibroids are noncancerous growths that can develop in the wall of a uterus. Different types of fibroids include intramural, submucosal, subserosal, and pedunculated. Intramural fibroids can occur within the muscular walls of the uterus and can cause heavy bleeding. Submucosal fibroids can occur inside the uterine cavity or can abut the uterine cavity. Submucosal fibroids can also cause heavy bleeding. Subserosal fibroids can occur on the outer wall of the uterus and can cause bulk or pressure symptoms. Pedunculated fibroids can attach to the uterine wall by a stalk-like growth called a peduncle.

When a patient has a submucosal fibroid, a hysteroscopic procedure can be used to examine the inside of the uterus and remove the fibroid via a hysteroscopic resection. A hysteroscope can be inserted through the vagina and through the natural opening of the cervix. Typically, due to the diameter of the hysteroscope, the cervix must be dilated, which can be painful and require the patient to be under general anesthesia. As a result, an operating room is required and the recovery period due to the dilation can be increased.

SUMMARY

Accordingly, what is needed is a smaller diameter hysteroscope that allows for less dilation of the cervix and less anesthesia. This problem can be addressed by providing a hysteroscope having an elongate member that includes first and second tracks. For example, the first and second tracks can include respective longitudinal lumens or working channels. A resection assembly can retract into and extend out from first and second tracks. The resection assembly can include a first member having a first portion located along the first track. The first member can function as a control member for the resection assembly. The resection assembly can also have a second member, which can function as a support member for the resection assembly. The second member can have a longitudinally axial fluid conduit passageway. The longitudinal passageway in the second member can be fluidly coupled with an irrigant source. This can permit irrigant to be provided to a target site via the longitudinal passageway in the support member. The second member can function as a support member for the resection assembly. The first and second tracks can have dual functionality. The first and second tracks can provide a structure for delivering the resection assembly to a target site. Moreover, one or both of the first and second tracks can provide irrigant to the target site.

The resection assembly can also an electrically activatable resection element and an electrically conductive stabilizing member. In a retracted position, the first and second members can be located inside the first and second tracks. In an extended position, distal portions of the first and second members can extend from the first and second tracks. In the extended position, the second member can provide irrigant to a target site via the longitudinally axial fluid conduit passageway. The first member can include an electrical insulator disposed around a portion of the electrically activatable resection element. The resection element can extend from the first member to form an electrically activatable resection loop. The first member can also include a conductive outer tube. The electrically activatable resection loop can extend from a distal end of the first member to the electrically conductive stabilizing member. The electrically conductive stabilizing member can extend between a distal end of the second member to the distal end of the first member.

The elongate member can also include a camera and a suction port. The electrically activatable resection loop can be oriented such that the electrically activatable resection loop is in a field of view of the camera and the suction port is above the camera. If bubbles form during use of the hysteroscope, with the suction port being above the camera, the suction port can pull the bubbles away from the camera field of view. This can help reduce or minimize an amount of bubbles that may otherwise obstruct the camera field of view.

A potential advantage includes the ability to reduce an amount of cervix dilation and patient anesthesia. More specifically, by providing a hysteroscope having dual function lumens that provide both a resection assembly and irrigation to a target site, an overall lateral size of the hysteroscope can be reduced, thereby reducing an amount by which the cervix should be dilated and potentially also reducing an amount of anesthesia necessary for a hysteroscopic procedure.

Another potential advantage relates to a device that can work in a small area by virtue of having a small size while having the ability remove large portions of tissue, such as large fibroids or large polyps.

A further potential advantage relates to enhancing a camera field of view by configuring the hysteroscope such that a suction port of the hysteroscope is above a camera of the hysteroscope thereby pulling bubbles formed during a hysteroscopic procedure away from the camera field of view.

DETAILED DESCRIPTION

A hysteroscope can include an elongate member that can includes first and second tracks (e.g., lumens or channels). A resection assembly can retract into and extend out from first and second tracks. The resection assembly can include a first member having a first portion located along the first track. The first member can function as a control member for the resection assembly. The resection assembly can also have a second "support" member having a longitudinally axial fluid conduit passageway. The longitudinal passageway of the second member can be fluidly coupled with an irrigant source. This can permit an irrigant to be provided to a target site via the longitudinal passageway in the support member. The second member can function as a support member for the resection assembly. The first and second tracks can have dual functionality. The first and second tracks can provide a structure for delivering the resection assembly to a target site. Moreover, one or both of the first and second tracks can provide irrigant to the target site.

Figure 1:
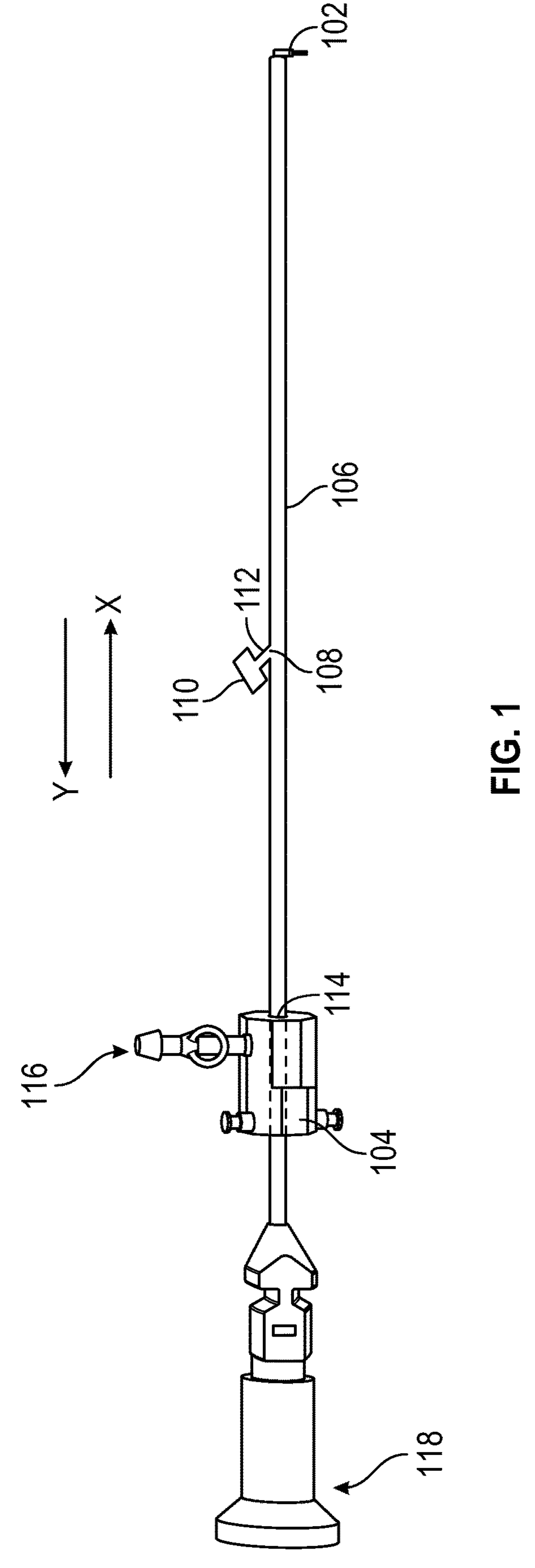
FIG. 1 illustrates a hysteroscope having a resection assembly.

FIG. 1 shows an example of a hysteroscope 100 having a resection assembly 102. While the hysteroscope 100 is shown as being a rigid hysteroscope, the hysteroscope 100 can also be a flexible type hysteroscope. The hysteroscope 100 can include a housing 104, which can function to receive various components of the hysteroscope 100. Examples of such components can include, but are not limited to, an endoscope, a light source, an inflow channel, and an outflow channel.

The hysteroscope 100 can also include an elongate member 106 extending from the housing 102. The elongate member 106 can include a lateral suction port 108 having a suction source connection 110. The suction source connection 110 can facilitate fluid coupling of the lateral suction port 108 with a suction source that can evacuate fluid from the lateral suction port 108. Thus, fluid and debris, such as material removed from a target site, can be removed from the target site and the hysteroscope 100 via the lateral suction port 108. In particular, fluid and debris can travel from the lateral suction port 108 along a suction port neck 112 to the suction source. While suction is described as occurring at the lateral suction port 108, suction can occur at different portions of the elongate member 106. For example, additionally or alternatively, the elongate member 106 can have a suction port located proximate a proximal end 114 of the elongate member 106.

The lateral suction port 108 can be used to remove irrigant provided to the elongate member 106 at an irrigation port 116 located at the elongate member proximal end 114. Irrigant can be provided to the elongate member from an irrigation source (not shown) that can be coupled to the irrigation port 116. The irrigant can be provided to a target site via the resection assembly 102.

Figure 2:
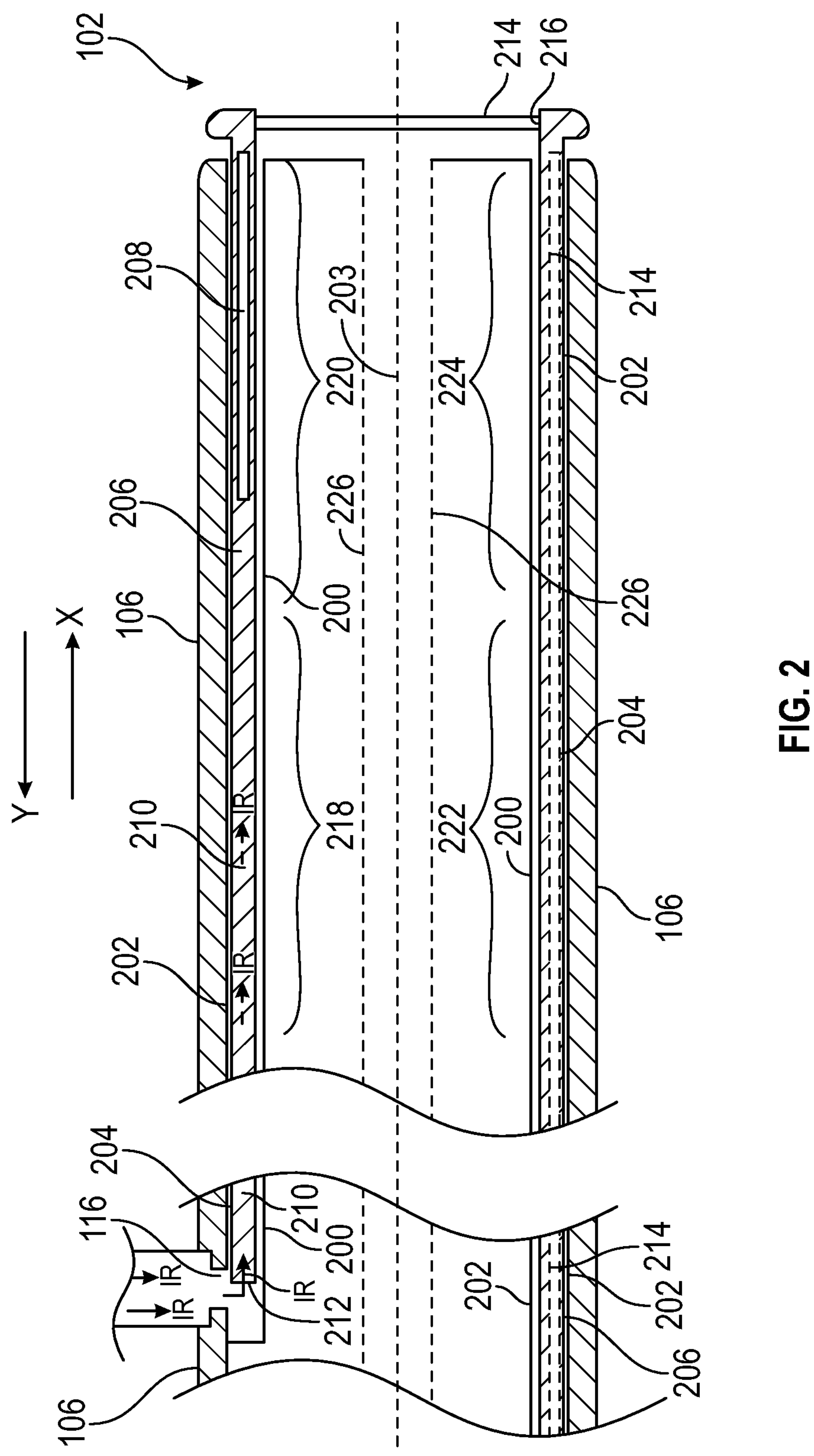
FIG. 2 shows an elongate member of the hysteroscope of FIG. 1.
Figure 3:
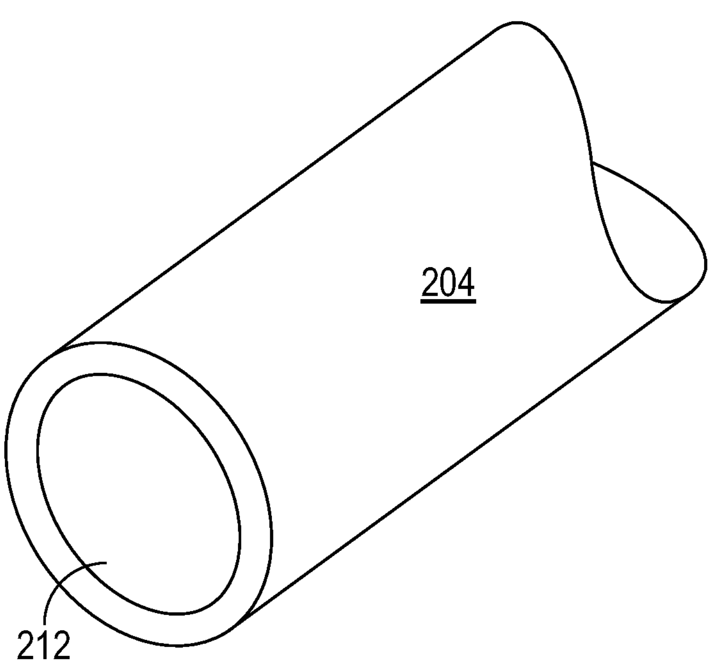
FIGS. 3 and 4 illustrate a second member of the resection assembly of FIG. 1.

The elongate member 106 can define both a first track 200 and a second track 202 along a longitudinal axis 203, such as shown in FIG. 2. A first member 204 of the resection assembly 102 can be located along the first track 200. The first member 204 can be a control member or a control arm. A second member 206 of the resection assembly 102 can be located along the second track 202. The second member 206 can be a support member or a support arm. The second member 206 can include a longitudinally axially fluid conduit passageway 208 through which irrigant ("IR") can be delivered to a target site. The second member 206 can define a second member lumen 210 where the longitudinally axially fluid conduit passageway 208 can open into the second member lumen 210. The second lumen member 210 can be in fluid communication with the irrigation port 116. The second member lumen 210 can extend to an opening 212 at a proximal end of the second member 206. The opening 212 is more clearly shown in FIG. 3. The second member opening 212 can be in close proximity to the irrigation port 116 such that irrigant IR that is provided from an irrigant source through the irrigation port 116 can travel into the second member opening 212. From the second member opening 212, the irrigant IR can travel through the second member lumen 210 and to the longitudinally axially fluid conduit passageway 208.

Figure 4:
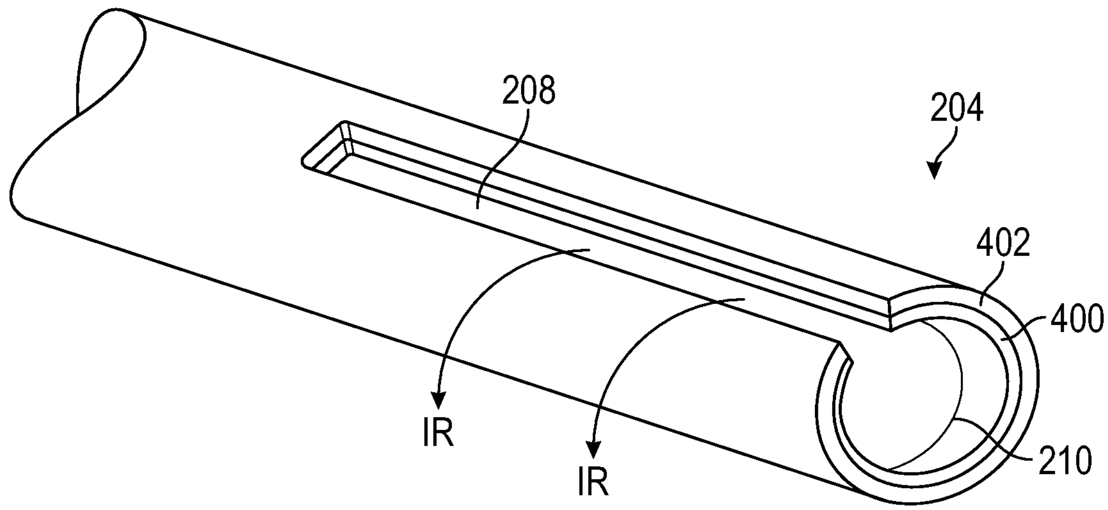

In FIG. 4, the longitudinally axially fluid conduit passageway 208 is in fluid communication with the second member lumen 210. By being in fluid communication with the second member lumen 210, which is in fluid communication with the irrigation port 116, the longitudinally axially fluid conduit passageway 208 is in fluid communication with the irrigation port 116. Thus, the irrigant IR can exit the second member lumen 210 via the longitudinally axially fluid conduit passageway 208 and to a target site. In FIG. 4, the second member 206 can be connected to ground. When the second member 206 is connected to ground, the second member 206 can include an insulator 400 disposed around the second member lumen 210 and a second member outer jacket 402 disposed around the insulator 400. The insulator 400 can be formed from any type of electrically insulative material, such as ceramic, any type of polymer, rubber, or the like. The second member outer jacket 402 can be formed from a conductive material and can function as a ground for an active resection element when the resection assembly 102 is being used to treat a target site. Examples of materials that can be used for the second member outer jacket 402 can include stainless steel, aluminum, copper, or the like.

Returning to FIG. 2, the resection assembly 102 can include an electrically activatable resection element 214 that can be disposed in, and extend through, the first member 204. The electrically activatable resection element 214 can be a conductor and extend from an electrical source (not shown) of the hysteroscope 100 to a distal end 216 of the first member 204. A portion of the electrically activatable resection element 214 can extend from the first member 204 at the first member distal end 216.

Figure 5:
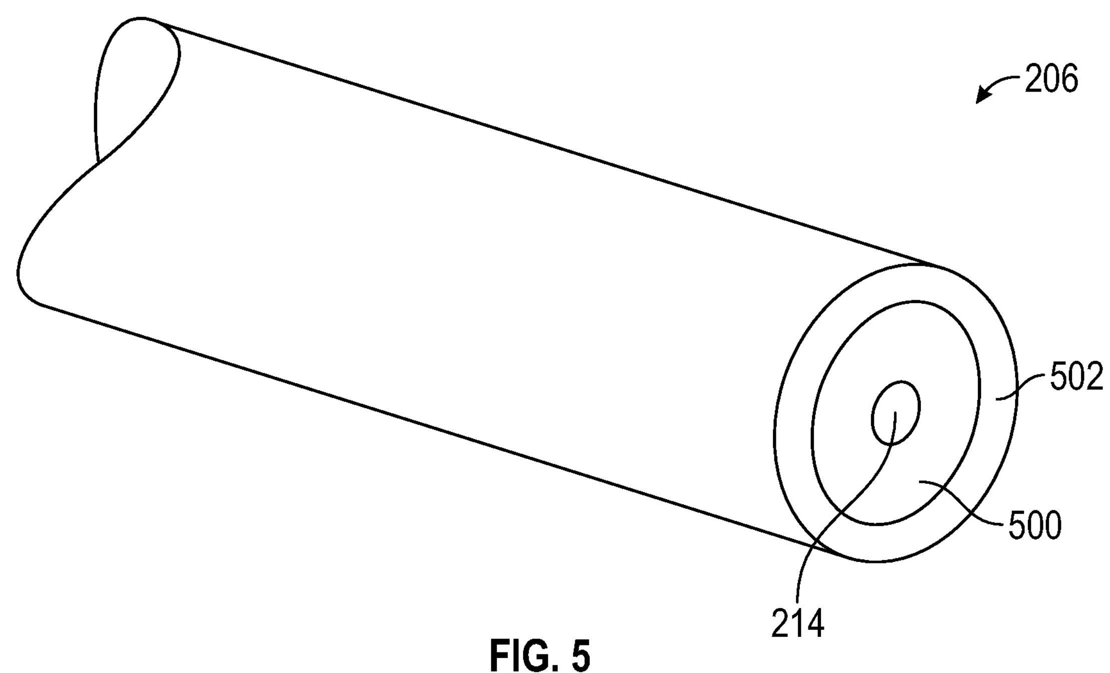
FIG. 5 illustrates a perspective view of the elongate member of FIG. 2.

In FIG. 5, the first member 204 can include an insulator 500 disposed around a portion of the electrically activatable resection element 214. The insulator 500 can be located inside a conductive outer tube 502 of the first member 204 and insulate the electrically activatable resection element 214 from the conductive outer tube 502. The insulator 500 can be formed from the same electrically insulative material as the insulator 400. The conductive outer tube 502 can be formed from the same conductive material as the second member outer jacket 402 and can be electrically coupled to ground in order to function as a ground for the electrically activatable resection element 214 when the resection assembly 102 is being used to treat a target site. The conductive outer tube 502 can also extend into the first track 200.

In FIGS. 1 and 2, the resection assembly 102 is shown in a retracted position, where the second member 206 and the first member 204 are substantially disposed inside the elongate member 106. The resection assembly 102 can be slidable along directions X and Y such that the resection assembly 102 can be in a retracted position and in an extended position. The first member 204 can be slidable in the first track 200 (e.g., lumen or channel) along the directions X and Y. Additionally, the second member 206 can be slidable in the second track 202 (e.g., lumen or channel) along the directions X and Y. In the retracted position, a first portion 218 of the second member 206 and a second portion 220 of the second member 206 can both be disposed along the first track 200. In the retracted position, a first portion 222 of the first member 204 and a second portion 224 of the first member 204 can both be disposed within the second track 202.

Figure 6:
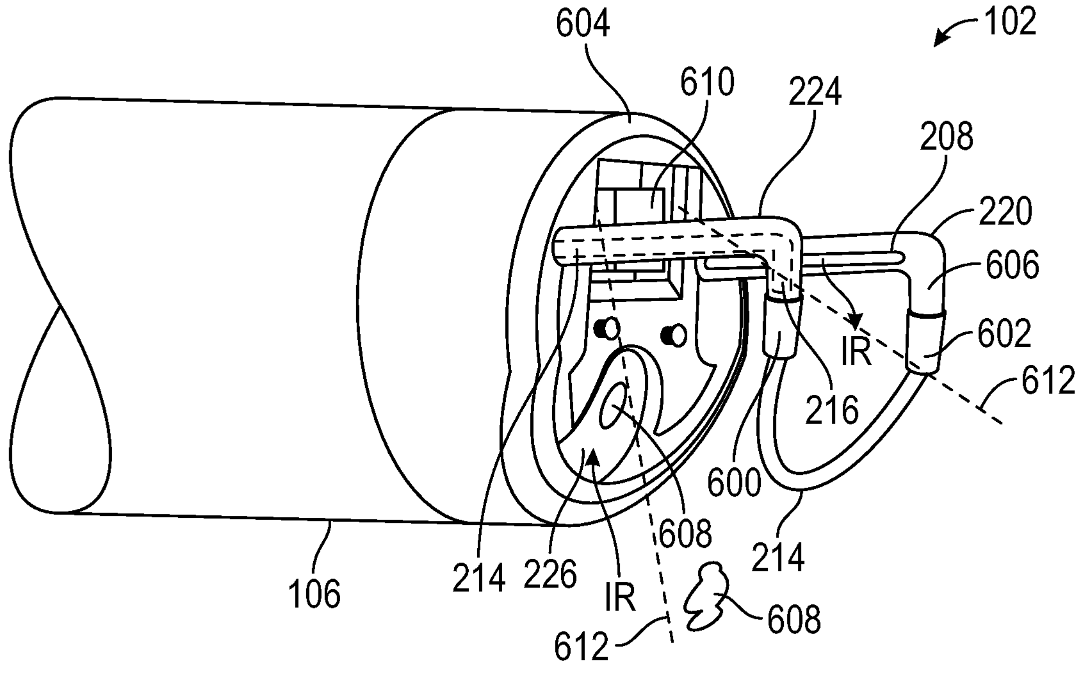
FIG. 6 illustrates a perspective view of the resection assembly extending from a distal end of the hysteroscope of FIG. 1.

In the extended position, the first portion 218 of the second member 206 can be disposed along the first track 200 while the second portion 220 of the second member 206 can extend distally from the elongate member 106, as shown in FIG. 6. In the extended position, the first portion 222 of the first member 204 can be disposed within the second track 202 while the second portion 224 of the first member 204 can extend distally from the elongate member 106, also as shown in FIG. 6.

The hysteroscope 100 can also include a handle 118. The handle 118 can be used to control a position of the resection assembly 102 from the retracted position of FIGS. 1 and 2 to an extended position of FIG. 6. In particular, the handle 118 can be moved along the direction X to move the resection assembly 102 into the position shown in FIG. 6 and along the direction Y to move the resection assembly 102 into the position shown in FIGS. 1 and 2. During a resection procedure, the resection assembly 102 can extend from the elongate member 106 in order to resect tissue from a tissue site.

The resection assembly 102 can also include a first electrical insulator 600 and a second electrical insulator 602. The first electrical insulator 600 can be disposed at the first member distal end 216. The second electrical insulator 602 can be disposed at a distal end 606 of the second member 206. The first electrical insulator 600 and the second electrical insulator 602 can be formed from the same electrically insulative material as the insulator 400. The electrically activatable resection element 214 can extend between the first electrical insulator 600 and the second electrical insulator 602 to form an electrically activatable resection loop as shown in FIG. 6.

The electrically activatable resection element 214 can be formed from any type of electrically conductive material, such as a copper wire, a nickel wire, an aluminum wire, a steel wire, or the like. The electrically activatable resection element 214 can be used to vaporize tissue at a target site during a resection procedure. Current can be provided to the electrically activatable resection element 214 from an electrical source in order to allow for vaporization during a resection procedure. The second member 206 can have the second member outer jacket 402 (FIG. 4) formed of an electrically conductive material as discussed above. Moreover, the second member outer jacket 402 can be electrically coupled to ground. The electrically activatable resection element 214 can electrically connect to the second member 206 and the second member outer jacket 402 thus providing a pathway for current provided to the electrically activatable resection element 214 during tissue vaporization.

During a resection procedure, the irrigant IR can be provided to the second member lumen 210 and delivered to the target site via the longitudinally axially fluid conduit passageway 208 as detailed above. As such, the hysteroscope 100 only requires a single member, the elongate member 106, which can deliver irrigant to a target site while also providing mechanism for resecting tissue at the target site.

The elongate member 106 can also include a distal suction port 226 which can fluidly couple with the lateral suction port 108. The distal suction port 226 can extend from a distal end 604 of the elongate member 106 to the lateral suction port 108. During a resection procedure, debris 608 and the irrigant IR can be pulled into the distal suction port 226 when suction is applied to the distal suction port 226. Thus, in addition to providing irrigant and a resection mechanism, a single member, such as the elongate member 106, can remove irrigant and debris from a target site during a resection procedure.

The hysteroscope 100 can include a camera 610 having a field of view 612 located at elongate member distal end 604. The resection assembly 102, and in particular the electrically activatable resection element 214, can be in the camera field of view 612. An operator of the hysteroscope 100 can view a target site along with the resection assembly 102 with the camera 610. During use of the hysteroscope 100, the operator can control resection using the electrically activatable resection element 214 with the handle 118 and the camera 610. As shown in FIG. 6, the camera 610 is located at an upper portion of the elongate member 106 while the suction passageway 226 is located at a lower portion of the elongate member 106 below the camera 610.

Figure 7:
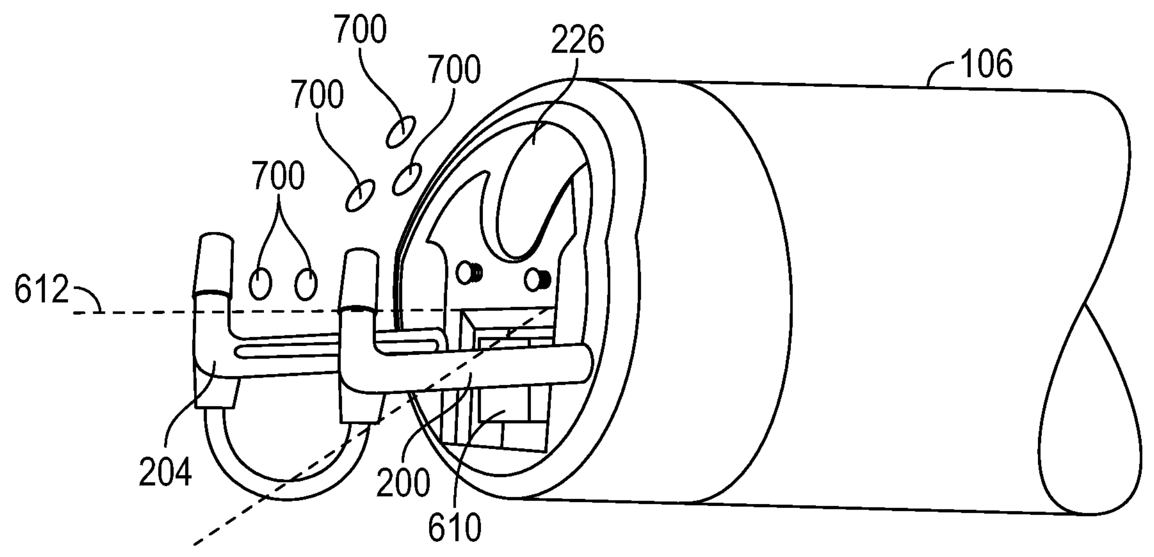
FIG. 7 shows an alternative example of a resection assembly.

Alternatively, the camera 610 can be located in a lower portion of the elongate member 106 while the suction passageway 226 is located at an upper portion of the elongate member 106 as shown in FIG. 7. Here, the suction passageway 226 is disposed above the camera 610. During resection at a target site, air bubbles 700 can form, which can obstruct the view of the camera 610 as the air bubbles 700 enter the camera field of view 612. By virtue of orienting the camera 610 below the suction passageway 226, the suction passageway can pull the air bubbles 700 out of the camera field of view 612, thereby providing a clearer camera field of view 612.

Figure 8:
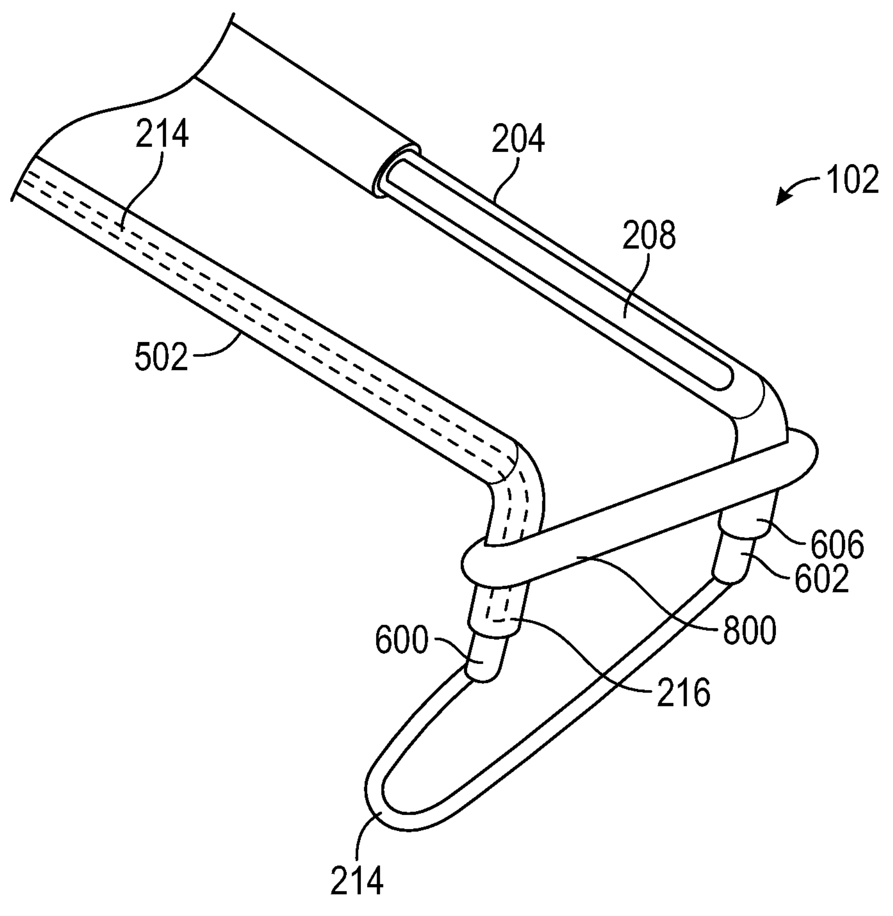
FIG. 8 illustrates a perspective view of the resection assembly of FIG. 1.

In the examples described above, the resection assembly 102 included the second member 206, the first member 204, the electrically activatable resection element 214, the first electrical insulator 600, and the second electrical insulator 602. A resection assembly can also include an electrically conductive stabilizing member 800 that extends between the first member distal end 216 and the support arm distal end 606, as shown in FIG. 8. As shown in FIG. 8, the resection assembly 102 includes the first electrical insulator 600 at the first member distal end 216 and the second electrical insulator 602 at the support arm distal end 606. The electrically conductive stabilizing member 800 can provide a pathway for current provided to the electrically activatable resection element 214 during tissue vaporization. The electrically conductive stabilizing member 800 can electrically connect to the conductive outer tube 502 thereby providing a pathway for current in the electrically activatable resection element 214 to ground.

Figure 9:
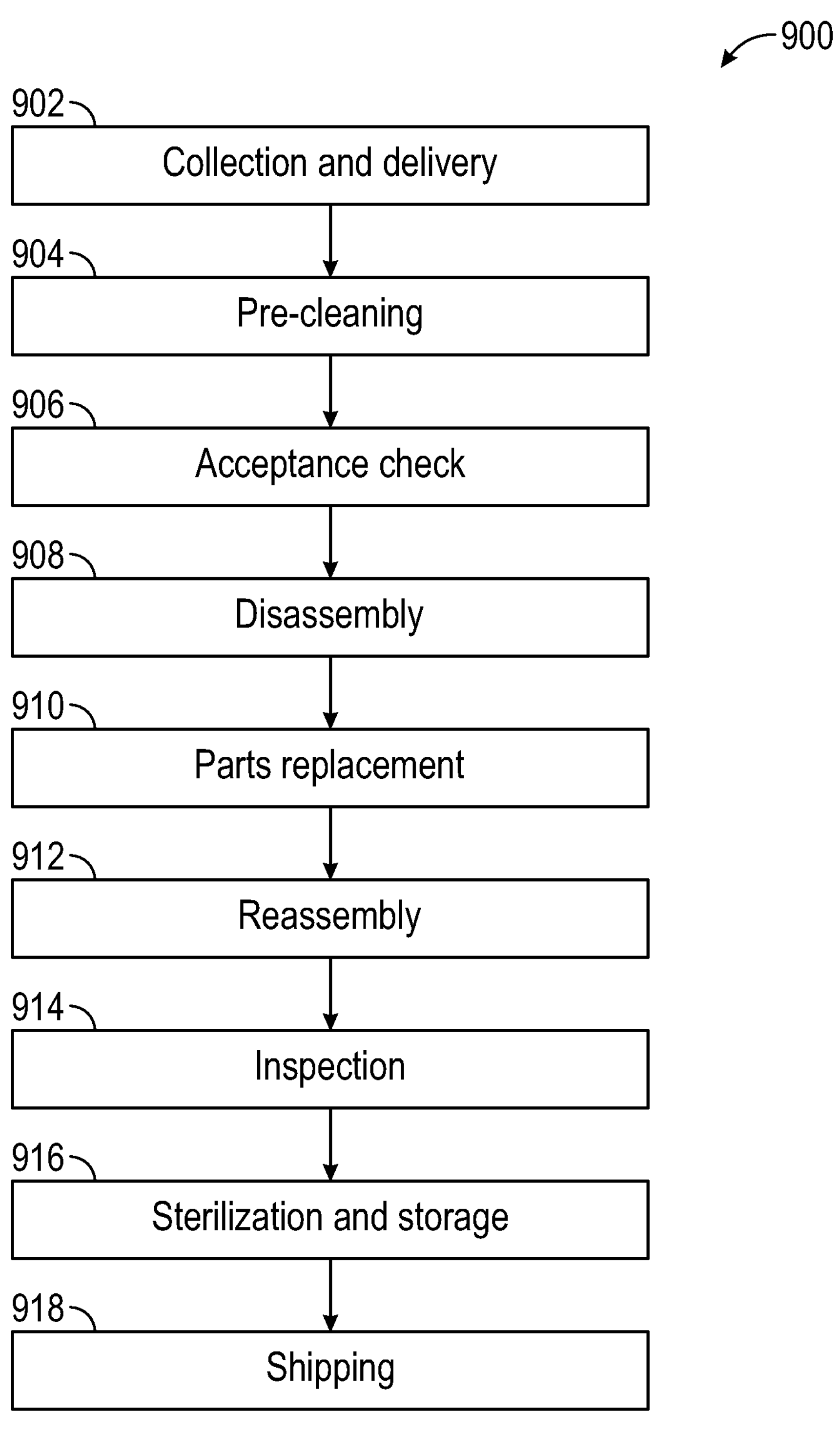
FIG. 9 is a flowchart indicating a reprocessing method for the hysteroscope of FIG. 1.

The hysteroscope 100 can be disposed of after a single use. Alternatively, the hysteroscope 100 can be repeatedly used a plurality of times. When the hysteroscope 100 can be repeatedly used a plurality of times, the hysteroscope 100 can be subjected to a method 900, as shown in FIG. 9, which is a flowchart illustrating a reprocessing method for the hysteroscope 100. The hysteroscope 100 described above may be disposed of after one use or may be repeatedly used a plurality of times. When repeatedly used a plurality of times, the reprocessing method in FIG. 9 can be used. An operator who remanufactures devices can collect the used hysteroscope 100 after it has been used for treatment and can transport the hysteroscope 100 to a factory or other facility at 902. The used hysteroscope 100 can be transported in a dedicated container such as to help prevent contamination from other treatments.

At 904, the operator cleans and sterilizes the used hysteroscope 100. During cleaning, deposits adhering to the portions of the hysteroscope 100 are removed by using a brush or the like. Any cleaning solution of isopropanol-containing cleaning agent, proteolytic enzyme detergent, and alcohol can be applied to the hysteroscope 100 in order to remove pathogenic microorganisms and the like derived from blood, body fluid, or the like. The cleaning agent is not limited to the cleaning liquid described above, and other cleaning agents can be used. During sterilization, high-pressure steam sterilization, ethylene oxide gas sterilization, gamma ray sterilization, hydrogen peroxide and hydrogen peroxide low temperature sterilization can be applied to the hysteroscope 100. By virtue of the hysteroscope 100 having the structures described above, the hysteroscope 100 is easy to clean.

After cleaning and sterilization, an acceptance check of the hysteroscope 100 can be performed at 906. During the acceptance check, an inspection of the hysteroscope 100 can be performed to determine if the hysteroscope 100 has any significant defects. Moreover, a number of times the hysteroscope 100 has been reprocessed can be determined. The number of times the hysteroscope 100 has been reprocessed can be compared against a threshold to determine if the number of times the hysteroscope 100 has been reprocessed exceeds a threshold and should no longer be used.

Next, at 908, the hysteroscope 100 can be disassembled where various components of the hysteroscope 100, such as the resection assembly 102 or the elongate member 106 are removed from the hysteroscope 100. While only the resection assembly 102 and the elongate member 106 are referenced as being removed, any portion of the hysteroscope 100 described herein can be removed at 908.

After disassembly at 908, any components of the hysteroscope 100 that are deemed defective can be replaced at 910. To further illustrate, if the resection assembly 102 is deemed defective, the resection assembly can be replaced at 910. While the resection assembly 102 is mentioned as being replaced, any portion of the hysteroscope 100 described herein can be replaced at 910.

After components of the hysteroscope 100 are replaced at 910, the hysteroscope 100 can be reassembled at 912. During reassembly, an identifier that can indicate the hysteroscope 100 has been modified from its original condition to include the replacement component(s) can be added. The identifier can include a label or any other type of indicia that designates the hysteroscope 100 as reprocessed, refurbished, or remanufactured.

The hysteroscope 100 is then inspected and tested at 914. Specifically, a user can verify that the newly formed hysteroscope 100 has the same effectiveness and safety as the original product by various functional tests. After inspection, the hysteroscope 100 can be sterilized and stored at 916. The hysteroscope 100 can be sterilized with a sterilizing gas such as ethylene oxide gas or propylene oxide gas. After sterilization, the hysteroscope 100 can be stored at 916 and then subsequently shipped at 918.

Having described various aspects and features of the inventive subject matter, the following numbered examples are provided as illustrative embodiments:

Example 1 is a medical device comprising: an elongate member defining a first track and a second track along a longitudinal axis of the elongate member; an irrigation port at a proximal end of the elongate member; and a resection assembly, extending from a distal end of the elongate member, the resection assembly including: a first member, including a first portion located along the first track; a second member having a longitudinally axial fluid conduit passageway, wherein the passageway is in fluid communication with the irrigation port, the second member having a first portion located along the second track; and an electrically activatable resection element extending from a distal end of the first member.

In Example 2, the subject matter of Example 1 includes, wherein the first member is slidable between a retracted position and an extended position along the first track, wherein the first portion of the first member and a second portion of the first member are located within the elongate member in the retracted position and the second portion extends distally from the elongate member in the extended position.

In Example 3, the subject matter of Examples 1-2 includes, wherein the second member is slidable between a retracted position and an extended position along the second track, wherein the first portion of the second member and a second portion of second member are located within the elongate member in the retracted position and the second portion extends distally from the elongate member in the extended position.

In Example 4, the subject matter of Examples 1-3 includes, the resection assembly further comprising: an electrically conductive stabilizing member that extends between a distal end of the first member and a distal end of the second member; a first electrical insulator located at the first member distal end; and a second electrical insulator located at the second member distal end, wherein the electrically activatable resection element extends between the first electrical insulator and the second electrical insulator to form an electrically activatable resection loop.

In Example 5, the subject matter of Example 4 includes, wherein the elongate member further comprises: a suction port at or extending from a distal end of the elongate member; and a camera located at the distal end of the elongate member, wherein the electrically activatable resection loop is located or movable to be within a field of view of the camera.

In Example 6, the subject matter of Examples 4-5 includes, the first member comprising: an electrically conductive outer tube extending into the first track; and an insulator located inside the conductive outer tube, wherein a portion of the electrically activatable resection element is located within the insulator.

In Example 7, the subject matter of Example 6 includes, wherein the electrically activatable resection element includes a portion of a conductor that extends from the first member.

In Example 8, the subject matter of Examples 6-7 includes, wherein the conductive outer tube of the first member is electrically coupled to a ground.

In Example 9, the subject matter of Examples 6-8 includes, wherein the second member includes an outer jacket formed from an electrically conductive material and the second member outer jacket is electrically coupled to a ground.

Example 10 is a method for processing an instrument for surgery, the method comprising: sterilizing a medical device comprising: an elongate member defining a first track and a second track along a longitudinal axis of the elongate member; an irrigation port at a proximal end of the elongate member; and a resection assembly, extending from a distal end of the elongate member, the resection assembly including: a first member, including a first portion located along the first track; a second member having a longitudinally axial fluid conduit passageway, wherein the passageway is in fluid communication with the irrigation port, the second member having a first portion located along the second track; and an electrically activatable resection element extending from a distal end of the first member; and storing the medical device in a sterile container.

Example 11 is a hysteroscope resection assembly comprising: a first member; a second member having a longitudinally axial fluid conduit passageway, wherein the second member defines a lumen and the passageway is in fluid communication with the second member lumen; and an electrically activatable resection element extending from a distal end of the first member.

In Example 12, the subject matter of Example 11 includes, an electrically conductive stabilizing member that extends between a distal end of the first member and a distal end of the second member; a first electrical insulator located at the first member distal end; and a second electrical insulator located at the second member distal end, wherein the electrically activatable resection element extends between the first electrical insulator and the second electrical insulator to form an electrically activatable resection loop.

In Example 13, the subject matter of Example 12 includes, the first member comprising: a conductive outer tube; and an insulator located inside the conductive outer tube, wherein a portion of the electrically activatable resection element is located within the insulator.

In Example 14, the subject matter of Example 13 includes, wherein the electrically activatable resection element includes a portion of a conductor that extends from the first member.

In Example 15, the subject matter of Examples 13-14 includes, wherein the conductive outer tube of the first member is electrically coupled to a ground.

In Example 16, the subject matter of Examples 13-15 includes, wherein the second member includes an outer jacket formed from an electrically conductive material and the second member outer jacket is electrically coupled to a ground.

Example 17 is a method for processing an instrument for surgery, the method comprising: sterilizing a hysteroscope comprising: a hysteroscope resection assembly comprising: a first member; a second member having a longitudinally axial fluid conduit passageway, wherein the second member defines a lumen and the passageway is in fluid communication with the second member lumen; and an electrically activatable resection element extending from a distal end of the first member; and storing the hysteroscope in a sterile container.

Example 18 is a medical device comprising: an elongate member defining a first track and a second track along a longitudinal axis of the elongate member, wherein the first track and the second track are configured to together provide a resection assembly to a target site and irrigant to the target site; an irrigation port at a proximal end of the elongate member; a suction port at or extending from a distal end of the elongate member; and a camera located at the distal end of the elongate member.

In Example 19, the subject matter of Example 18 includes, wherein the second track is in fluid communication with the irrigation port and wherein the suction port is located in a first lateral portion of the distal end of the elongate member and the camera is located in an opposing second lateral portion of the distal end of the elongate member below the suction port.

Example 20 is a method for processing an instrument for surgery, the method comprising: sterilizing a medical device comprising: an elongate member defining a first track and a second track along a longitudinal axis of the elongate member, wherein the first track and the second track are configured to together provide a resection assembly to a target site and irrigant to the target site; an irrigation port at a proximal end of the elongate member; a suction port at or extending from a distal end of the elongate member; and a camera located at the distal end of the elongate member; and storing the medical device in a sterile container.

Example 21 is at least one machine-readable medium including instructions that, when executed by processing circuitry, cause the processing circuitry to perform operations to implement of any of Examples 1-20.

Example 22 is an apparatus comprising means to implement of any of Examples 1-20.

Example 23 is a system to implement of any of Examples 1-20.

Example 24 is a method to implement of any of Examples 1-20.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A medical device comprising:

an elongate member defining a first track and a second track along a longitudinal axis of the elongate member;

an irrigation port at a proximal end of the elongate member; and a resection assembly extending from a distal end of the elongate member, the resection assembly including:

a first member, including a first portion located along the first track;

a second member having a longitudinally axial fluid conduit passageway, wherein the longitudinally axial fluid conduit passageway is in fluid communication with the irrigation port, the second member having a first portion located along the second track;

an electrically activatable resection element extending from a distal end of the first member;

an electrically conductive stabilizing member that extends between the distal end of the first member and a distal end of the second member;

a first electrical insulator located at the first member distal end; and a second electrical insulator located at the second member distal end, wherein the electrically activatable resection element extends between the first electrical insulator and the second electrical insulator.

2. The medical device of claim 1, wherein the first member is slidable between a retracted position and an extended position along the first track, wherein the first portion of the first member and a second portion of the first member are located within the elongate member in the retracted position and the second portion extends distally from the elongate member in the extended position.

3. The medical device of claim 1, wherein the second member is slidable between a retracted position and an extended position along the second track, wherein the first portion of the second member and a second portion of second member are located within the elongate member in the retracted position and the second portion extends distally from the elongate member in the extended position.

4. The medical device of claim 1, wherein the electrically activatable resection element forms an electrically activatable resection loop.

5. The medical device of claim 4, wherein the elongate member further comprises:

a suction port at or extending from a distal end of the elongate member; and a camera located at the distal end of the elongate member, wherein the electrically activatable resection loop is located or movable to be within a field of view of the camera.

6. The medical device of claim 4, the first member comprising:

an electrically conductive outer tube extending into the first track; and an insulator located inside the electrically conductive outer tube, wherein a portion of the electrically activatable resection element is located within the insulator.

7. The medical device of claim 6, wherein the electrically activatable resection element includes a portion of a conductor that extends from the first member.

8. The medical device of claim 6, wherein the conductive outer tube of the first member is electrically coupled to a ground.

9. The medical device of claim 6, wherein the second member includes an outer jacket formed from an electrically conductive material and the second member outer jacket is electrically coupled to a ground.

10. The medical device of claim 1, wherein the first track and the second track are configured to together provide the resection assembly to a target site and irrigant to the target site;

a suction port at or extending from a distal end of the elongate member; and a camera located at the distal end of the elongate member.

11. The medical device of claim 10, wherein the second track is in fluid communication with the irrigation port and wherein the suction port is located in a first lateral portion of the distal end of the elongate member and the camera is located in an opposing second lateral portion of the distal end of the elongate member.

12. A medical device comprising:

an elongate member defining a first track and a second track along a longitudinal axis of the elongate member;

an irrigation port at a proximal end of the elongate member; and a resection assembly extending from a distal end of the elongate member, the resection assembly including:

a first member, including a first portion located along the first track;

a second member having a longitudinally axial fluid conduit passageway, wherein the longitudinally axial fluid conduit passageway is in fluid communication with the irrigation port, the second member having a first portion located along the second track;

an electrically activatable resection element extending from a distal end of the first member;

an electrically conductive stabilizing member that extends between the distal end of the first member and a distal end of the second member;

a first electrical insulator located at the first member distal end; and a second electrical insulator located at the second member distal end, wherein the electrically activatable resection element extends between the first electrical insulator and the second electrical insulator to form an electrically activatable resection loop.

13. The medical device of claim 12, wherein the first member is slidable between a retracted position and an extended position along the first track, wherein the first portion of the first member and a second portion of the first member are located within the elongate member in the retracted position and the second portion extends distally from the elongate member in the extended position.

14. The medical device of claim 12, wherein the second member is slidable between a retracted position and an extended position along the second track, wherein the first portion of the second member and a second portion of second member are located within the elongate member in the retracted position and the second portion extends distally from the elongate member in the extended position.

* * * * *